(12) United States Patent
Melder

(10) Patent No.: US 7,753,962 B2
(45) Date of Patent: Jul. 13, 2010

(54) TEXTURED MEDICAL DEVICES

(75) Inventor: Robert Melder, Santa Rosa, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 379 days.

(21) Appl. No.: 11/668,708

(22) Filed: Jan. 30, 2007

(65) Prior Publication Data

US 2008/0183276 A1 Jul. 31, 2008

(51) Int. Cl.
*A61F 2/28* (2006.01)
*A61F 2/06* (2006.01)

(52) U.S. Cl. ............... 623/23.59; 623/1.46; 623/23.36

(58) Field of Classification Search ........ 623/1.11–1.46
See application file for complete search history.

(56) References Cited

U.S. PATENT DOCUMENTS

| | | | |
|---|---|---|---|
| 4,795,472 A * | 1/1989 | Crowninshield et al. | 623/23.29 |
| 4,882,245 A | 11/1989 | Gelorme et al. | |
| 4,955,907 A * | 9/1990 | Ledergerber | 623/8 |
| 5,362,718 A | 11/1994 | Skotnicki et al. | |
| 5,947,893 A * | 9/1999 | Agrawal et al. | 600/36 |
| 6,015,815 A | 1/2000 | Mollison | |
| 6,329,386 B1 | 12/2001 | Mollison | |
| 6,569,195 B2 * | 5/2003 | Yang et al. | 623/1.46 |
| 6,979,346 B1 | 12/2005 | Hossainy et al. | |
| 7,041,127 B2 * | 5/2006 | Ledergerber | 623/1.31 |
| 7,077,867 B1 * | 7/2006 | Pope et al. | 623/20.14 |
| 7,083,642 B2 * | 8/2006 | Sirhan et al. | 623/1.42 |
| 7,273,493 B2 * | 9/2007 | Ledergerber | 623/1.13 |
| 2001/0039454 A1 * | 11/2001 | Ricci et al. | 623/23.5 |
| 2006/0083772 A1 | 4/2006 | DeWitt et al. | |
| 2009/0076591 A1 * | 3/2009 | Girton et al. | 623/1.16 |
| 2009/0204226 A1 * | 8/2009 | Fonte | 623/23.15 |
| 2009/0264975 A1 * | 10/2009 | Flanagan et al. | 623/1.2 |
| 2009/0306676 A1 * | 12/2009 | Lang et al. | 606/102 |
| 2010/0106234 A1 * | 4/2010 | Melder | 623/1.11 |

FOREIGN PATENT DOCUMENTS

| | | |
|---|---|---|
| EP | 1475053 | 11/2004 |
| WO | WO2007/095549 | 8/2007 |

* cited by examiner

*Primary Examiner*—Suzette J Gherbi

(57) ABSTRACT

Disclosed are medical devices having textured surfaces and biocompatible coatings disposed thereon. The textured surfaces allow for durable coatings to be applied to the medical device without a previous pre-coating having been applied. The biocompatible coating can further comprise a bioactive agent.

23 Claims, 1 Drawing Sheet

TEXTURED MEDICAL DEVICES

FIELD OF THE INVENTION

The present invention pertains to medical devices having textured surfaces and coatings disposed thereon.

BACKGROUND OF THE INVENTION

The pursuit of surgical solutions in anatomical defects has provided implantable medical devices. Vascular stents are used to restore patency to plaque-ridden arteries, pacemakers supply electrical signals to damaged heart tissues, bone screws support fragile fractures, and synthetic cardiac valves replace damaged or diseased ones, and these are just a few examples of life-altering medical devices. Implantable medical devices such as these have enhanced the lives of many patients and are conducive to minimally invasive surgical procedures. For example, drug-eluting implantable medical devices such as vascular stents have been developed to provide in situ controlled release or drugs such as heparin, rapamycin, and taxol.

However, implantable medical devices may have adverse consequences for the body. For example, a medical device may migrate from the initial implantation site resulting in loss of efficacy or serious injury. Polished bare metal stents may migrate before endothelialization can occur and exacerbate the initial restriction in coronary blood flow. Moreover, directly coating polished bare metal stents with drugs can result in an immediate release of the drug rather than controlled release. As a result the drug's beneficial effects are diminished, or in some cases localized drug toxicity may occur.

An innovative solution to combat the aforementioned problems with polished bare metal medical devices, particularly vascular stents, has been the development of coating technologies. Polymeric coatings, both bioresorbable and non-bioresorbable are applied directly to the stent surface using methods including, but not limited to, spraying, brushing and rolling techniques. The coating can increase the stents biocompatibility and provide a more adhesive stent surface to prevent migration. Furthermore, polymer coating may also have drugs incorporated into the coating to provide the patient with a controlled-release medical device to prevent or treat conditions such as restenosis. Metals and other non-polymers can also be applied to the surface of a medical device. These materials are usually deposited on the device's surface using chemical vapor deposition (CVD) or chemical solution deposition (CSD). However, coatings applied directly to the surface of a polished bare metal device can delaminate; this is especially true for polymers. Delamination can result in unwanted thrombogenic events that may require more aggressive, invasive procedures to correct.

One solution to problems with delamination is to first apply an undercoat or primer to the medical device surface to enhance the durability of the final coating polymer by increasing the adhesion of the coating to the metal or other medical device material. However, the use of a primer introduces another foreign material into the patient and, if not biodegradable, may be left behind as a residue following the biodegradation or bio-corrosion of the medical device substrate.

One possible solution that will minimize the aforementioned problems is to provide the implantable medical device with a roughened or textured surface. The elimination of smooth surfaces provides additional surface area for the adhesion of polymers and endothelial cells and provides for superior controlled release of therapeutic agents. Moreover, coatings applied to textured medical devices surfaces are less likely to delaminate.

Textured surfaces enhance controlled drug delivery by providing reservoirs for drugs and thus increase the amount of therapeutic compound that can be loaded onto the device's surface. This in turn increases the time required for physiological fluids to penetrate the device surface and transport the therapeutic compound into the blood stream or adjacent tissue. Moreover, recently titanium provided with textured surfaces has been shown to endothelialize more rapidly and with greater affinity than non-textured titanium surfaces.

Thus there remains a need to improve medical device performance by providing medical devices with textured surfaces.

SUMMARY OF THE INVENTION

The present invention provides for medical devices having textured surfaces which allow stronger adhesion of coatings thereby decreasing the risk of coating delamination. The textured surface comprises closely spaced regular or random grooves forming a geometric pattern distributed over at least a portion of the area to be coated.

In one embodiment of the present invention, a medical device is provided comprising a textured surface and a biocompatible coating disposed on said textured surface.

In another embodiment, the textured surface comprises closely spaced regular or random grooves forming a geometric pattern. In another embodiment, the geometric pattern comprises the pattern of FIG. 1. In another embodiment, the geometric pattern comprises the pattern of FIG. 2. In yet another embodiment, the geometric pattern is random and irregular and comprises the pattern of FIG. 3.

In another embodiment of the present invention, the textured surface comprises less than 100% of the medical device surface. In another embodiment, the textured surface comprises less than 50% of the medical device surface. In still another embodiment, the textured surface comprises more than one discontinuous area of textured surface.

In yet another embodiment of the present invention, the biocompatible coating further comprises at least one bioactive agent. In another embodiment, the at least one bioactive agent is selected from the group consisting of anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. In another embodiment, the at least one bioactive agent is selected from the group consisting of sirolimus (rapamycin), tacrolimus (FK506), everolimus (certican), temsirolimus (CCl-779) and zotarolimus (ABT-578).

In one embodiment, the textured surface is prepared by a process selected from the group consisting of chemical etching, plasma etching, mechanical etching, and photo-etching.

In another embodiment, the biocompatible coating comprises a polymer. In another embodiment, the polymer is selected from the group consisting of polyvinyl pyrrolidone, polytetrafluoroethylene, poly-L-lactic acid, polycaprolactone, polyethylene glycol, polystyrene, acrylates, polyethers, polyurethanes, polyamides, polyesters, epoxies, silicones, cellulose, and derivatives, and combinations thereof.

In yet another embodiment of the present invention, the medical device is selected from the group consisting of vascular stents, urethral stents, pacemakers, implantable defibrillators, bone screws, guide wires, dental implants, vascular stents, stent grafts, urethral stents, bile duct stents, catheters, pacemaker leads, sutures and prosthetic heart valves. In one embodiment, the medical device is a vascular stent.

In another embodiment of the present invention, the medical device does not have a primer coat between the medical device substrate and the biocompatible coating.

DEFINITION OF TERMS

Figure 1:
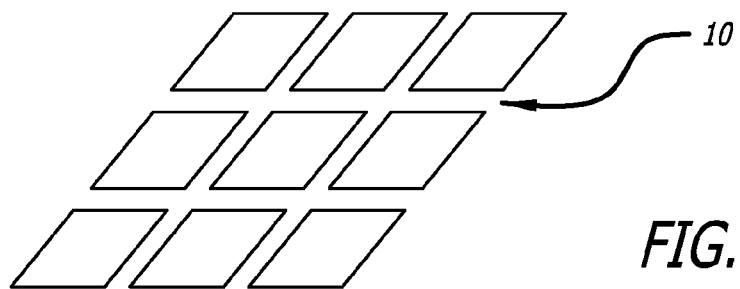
FIG. 1 depicts an exemplary geometric pattern for a textured medical device surface according to the teachings of the present invention.

Biocompatible: As used herein "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Bioactive Agent(s): As used herein, "bioactive agent" shall include any compound or drug having a therapeutic effect in an animal. Exemplary, non limiting examples include anti-proliferatives including, but not limited to, macrolide antibiotics including FKBP-12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. Drugs can also refer to bioactive agents including anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

Exemplary FKBP-12 binding agents include sirolimus (rapamycin), tacrolimus (FK506), everolimus (certican or RAD-001), temsirolimus (CCl-779 or amorphous rapamycin 42-ester with 3-hydroxy-2-(hydroxymethyl)-2-methylpropionic acid as disclosed in (USPASN) U.S. patent application Ser. No. 10/930,487) and zotarolimus (ABT-578; see (USPN) U.S. Pat. Nos. 6,015,815 and 6,329,386). Additionally, and other rapamycin hydroxyesters as disclosed in U.S. Pat. No. 5,362,718 may be used in combination with the coating polymers of the present invention.

Photo etching: As used herein "photo etching" refers to a surface texturing process involving the use of light as part of the texturing procedure.

Photoresist: As used herein "photoresist" refers to a photo-activated chemical compound that is resistant to etching compounds.

DETAILED DESCRIPTION OF THE INVENTION

The present invention provides for medical devices having textured surfaces which allow stronger adhesion of coatings thereby decreasing the risk of coating delamination. The textured surface comprises closely spaced regular grooves forming a geometric pattern distributed over at least a portion of the area to be coated. The textured surface increases the contact area with the coating and provides resistance to polymer flaking and peeling resulting from tangential and other disruptive mechanical forces. Furthermore, in one embodiment, the textured surface comprises a geometric pattern and is oriented along multiple geometric planes. Such oriented geometric patterning resists propagation of interfacial separation.

The geometric patterning on the surface of the medical device is prepared by methods including, but not limited to, chemical etching, photo-etching, mechanical etching, and plasma etching.

Textured surfaces can be created on medical devices manufactured from a variety of materials including, but not limited to, metals, metal alloys, polymers, ceramics, and derivatives, and combinations thereof. Suitable metallic alloys include, but are not limited to, alloys of magnesium, calcium, iron, nickel, titanium, cobalt, manganese, zinc, and other transition and non-transition metals. Suitable polymers include, but are not limited to acrylates, polyethers, polyesters, polyurethanes, polyamides, and derivatives and combinations thereof.

In one embodiment the medical device is textured using plasma. Suitable plasma texturing processes include, but are not limited to, vacuum plasma spraying (VPS), reactive ion plasma etching, sputtering, chemical vapor deposition (CVD), and combinations thereof. Medical devices suitable for plasma-etching include, but are not limited to, medical devices manufactured from metals, metal alloys, polymers, ceramics, and derivatives, and combinations thereof.

In another embodiment, the medical device is textured using mechanical etching processes. Mechanical etching comprises precisely controlled multi-axis machine tools and milling cutters to remove, in a controlled fashion, a predetermined amount of material from a surface. Medical devices suitable for mechanical etching include, but are not limited to, medical devices fabricated from metals, metal alloys and polymers.

In yet another embodiment, the medical device is textured using chemical etching processes. The chemical etching processes include wet and dry etching. Wet etching involves the immersion of the medical device in an etching solution that will partly dissolve the surface of the medical device. Dry etching, on the other hand, involves treating the medical device with a reactive chemical vapor to texture the surface. Medical devices conducive to wet or dry etching include, but are not limited to, medical devices fabricated from metals, metal alloys, and polymers.

In another embodiment, the medical device is textured using photo-etching processes. Photo-etching is a process using photographic techniques. The most common type of photo-etching involves a material that is photosensitive and resistant to acids or other etching compounds. This material, known as a photoresist, is applied to a substrate to be photo-etched. The substrate is then exposed to light and the photoresist reacts either with itself (polymerized) or with the substrate (at only the contact points) or both the contact points and itself. Then the substrate is etched with the appropriate etching chemical and the photoresist removed. Photoresist techniques include both positive and negative photo-etching. In one embodiment, the photoresist materials comprise a combination of diazonaphthoquinone (DNQ) and Novolac resin (a phenol formaldehyde resin), SU-8 resins (U.S. Pat. No. 4,882,245 which is hereby incorporated by reference), and other photo-activated chemical compounds. The photoresist is then exposed to light through a photographic negative causing it to harden where the negative allows light to pass. The photoresist is then developed by washing in a solvent that removes the unhardened parts. Finally, the material to be etched is exposed to an acid or other etching compound which dissolves the exposed parts of the material.

Many permutations in photo-etching processes are possible. Etching compounds include, but are not limited to, acids, bases, oxidizers, reductive compounds, reactive compounds, and derivatives and combinations thereof. Photoresists include, but are not limited to chromophores, diazonaphtoquinone, aromatic compounds, polystyrene polymers, and derivatives and combinations thereof.

In one non limiting photoetching method, textured medical devices with deep engraving having sloped shoulders on the substrate are produced. In this method the medical device is held in a mixture of etching compounds and an organic oil is splashed onto the medical device. As the etching compounds etch the surface of the medical device, the oil adheres to the edges of the exposed area. This progressively reduces the area being etched resulting in a sloped edge; a single dot will end up as a cone-shaped mound protruding from the etched area.

Figure 2:
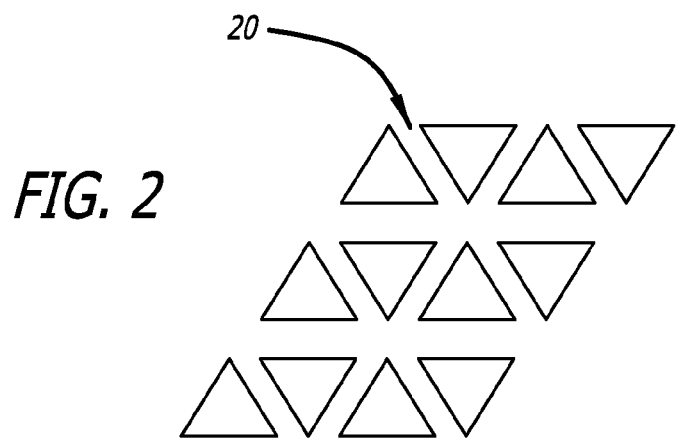
FIG. 2 depicts an exemplary geometric pattern for a textured medical device surface according to the teachings of the present invention.
Figure 3:
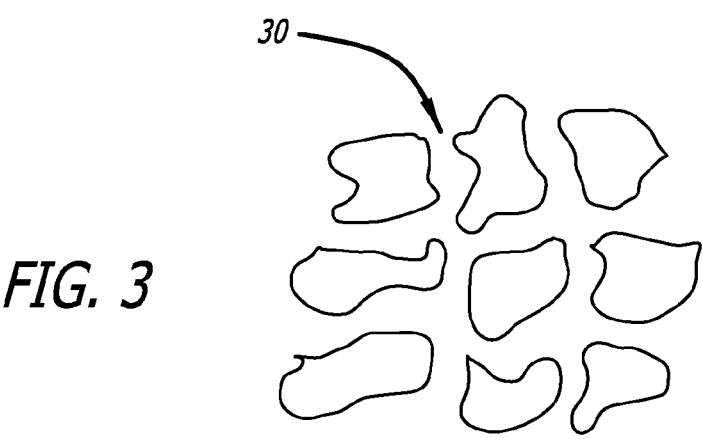
FIG. 3 depicts an exemplary geometric pattern for a textured medical device surface according to the teachings of the present invention.

In one embodiment, the textured surface comprises a regular and repeating two-dimensional geometry. Non-limiting, exemplary geometries are described in FIGS. 1-3. In one embodiment, the shapes of the etchings may also be 2-D closed, non-angled geometries. Selection of shape and gap (etch width) size of the geometric forms can be varied to optimize the coating efficiency base on the coating polymer's viscosity and the ability of the polymer to coat the surface without gaps or bubbles. FIG. 1 depicts one embodiment of the texturing geometry of the present invention consisting of repeating parallelogram shaped units having a fixed etch width 10. FIG. 2 depicts one embodiment of the texturing geometry of the present invention consisting of repeating triangular shaped units having a fixed etch width 20. FIG. 3 depicts one embodiment of the texturing geometry of the present invention consisting of repeating irregularly shaped units having an etch width 30.

In one embodiment of the present invention, the textured area comprises only a portion of the medical device surface. In one embodiment, the textured are comprises less 100% of the total medical device surface. In another embodiment, the textured area comprises less than 50% of the total medical device surface. In another embodiment, the textured area comprises less than 25% of the total medical device surface. In another embodiment, the medical comprises more than one textured area discontinuous with each other.

In one embodiment of the present invention, a medical device is textured and coated without an undercoat or a primer.

The textured medical devices of the present invention are able to receive biocompatible polymeric coatings without a pre-treatment such as a primer or an undercoat. The textured surface of the medical device prevents delamination of the polymer coating by providing a large surface for the polymer to adhere to.

Polymeric coatings of the present invention include, but are not limited to polymers, ceramics, controlled release polymers, biocompatible compounds, and derivatives and combinations thereof. In one embodiment, the coatings comprise biocompatible polymers (bioerodable, bioresorbable or non-erodable) such as, but not limited to, polyvinyl pyrrolidone, polytetrafluoroethylene, poly-L-lactic acid, polycaprolactone, polyethylene glycol, polystyrene, acrylates, polyethers, polyurethanes, polyamides, polyesters, epoxies, silicones, cellulose, and derivatives, and combinations thereof.

The medical devices of the present invention include, but are not limited to vascular stents, urethral stents, pacemakers, implantable defibrillators, bone screws, guide wires, dental implants, vascular stents, stent grafts, urethral stents, bile duct stents, catheters, pacemaker leads, sutures and prosthetic heart valves. In one embodiment, the medical device is a vascular stent.

In one embodiment of the present invention, the polymeric coating further comprises at least one bioactive agent controllably released from the coating polymer. Bioactive agents suitable for controlled release from the medical devices of the present invention include, but are not limited to, anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. Exemplary FKBP-12 binding agents include sirolimus (rapamycin), tacrolimus (FK506), everolimus (certican or RAD-001), zotarolimus (ABT-578; see U.S. Pat. Nos. 6,015,815 and 6,329,386), rapamycin 42-ester with 3-hydroxy-2-(hydroxymethyl)-2-methylpropionic acid (either amorphous or crystalline; temsirolimus (CCI-779)), as disclosed in U.S. patent application Ser. No. 10/930,487 and other rapamycin hydroxyesters as disclosed in U.S. Pat. No. 5,362,718. The entire contents of all of preceding patents and patent applications are herein incorporated by reference for all they teach related to FKBP-12 binding compounds and their derivatives.

EXAMPLES

Example 1

Texturing a Stent by Photo-Etching

An acid resistant photoresist is applied to a metallic stent in a regular pattern and exposed to light. The stent is then washed with the appropriate solvent to remove uncured photoresist. The stent is then dipped in a solution of nitric acid for 5 minutes and removed. The stent is then washed with a saturated solution of $NaHCO_3$ and allowed to dry.

Example 2

Coating a Textured Stent

A solution of a coating polymer and optionally a bioactive agent are mixed in a solvent such as chloroform or tetrahydrofuran and the coating mixture is sprayed onto the textured stent of Example 1. The stents is then allowed to dry producing a controlled release coating on the vascular stent.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Certain embodiments of this invention are described herein, including the best mode known to the inventors for carrying out the invention. Of course, variations on those embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A medical device comprising a textured surface and a biocompatible polymeric coating disposed on said textured surface, wherein said textured surface comprises closely spaced regular grooves forming a geometric pattern comprising repeating parallelogram shaped units having a fixed etch width.

2. The medical device of claim 1 wherein said textured surface comprises less than 100% of the medical device surface.

3. The medical device of claim 2 wherein said textured surface comprises less than 50% of the medical device surface.

4. The medical device of claim 1 wherein said textured surface comprises more than one discontinuous area of textured surface.

5. The medical device of claim 1 wherein said polymer is selected from the group consisting of polyvinyl pyrrolidone, polytetrafluoroethylene, poly-L-lactic acid, polycaprolactone, polyethylene glycol, polystyrene, acrylates, polyethers, polyurethanes, polyamides, polyesters, epoxies, silicones, cellulose, and derivatives, and combinations thereof.

6. The medical device of claim 1 wherein said biocompatible coating further comprising at least one bioactive agent.

7. The medical device of claim 6 wherein said at least one bioactive agent is selected from the group consisting of anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids.

8. The medical device of claim 7 wherein said at least one bioactive agent is selected from the group consisting of sirolimus (rapamycin), tacrolimus (FK506), everolimus (certican), temsirolimus (CCI-779) and zotarolimus (ABT-578).

9. The medical device of claim 1 wherein said medical device is selected from the group consisting of vascular stents, urethral stents, pacemakers, implantable defibrillators, bone screws, guide wires, dental implants, vascular stents, stent grafts, urethral stents, bile duct stents, catheters, pacemaker leads, sutures and prosthetic heart valves.

10. The medical device of claim 9 wherein said medical device is a vascular stent.

11. The medical device of claim 1 wherein said textured surface is prepared by a process selected from the group consisting of chemical etching, plasma etching, mechanical etching, and photo-etching.

12. The medical device of claim 1 wherein said medical device does not have a primer coat.

13. A medical device comprising a textured surface and a biocompatible polymeric coating disposed on said textured surface, wherein said textured surface comprises closely spaced regular grooves forming a geometric pattern, comprising repeating triangular shaped units having a fixed etch width.

14. The medical device of claim 13 wherein said textured surface comprises less than 100% of the medical device surface.

15. The medical device of claim 14 wherein said textured surface comprises less than 50% of the medical device surface.

16. The medical device of claim 13 wherein said textured surface comprises more than one discontinuous area of textured surface.

17. The medical device of claim 13 wherein said polymer is selected from the group consisting of polyvinyl pyrrolidone, polytetrafluoroethylene, poly-L-lactic acid, polycaprolactone, polyethylene glycol, polystyrene, acrylates, polyethers, polyurethanes, polyamides, polyesters, epoxies, silicones, cellulose, and derivatives, and combinations thereof.

18. The medical device of claim 13 wherein said biocompatible coating further comprising at least one bioactive agent.

19. The medical device of claim 18 wherein said at least one bioactive agent is selected from the group consisting of anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids.

20. The medical device of claim 19 wherein said at least one bioactive agent is selected from the group consisting of sirolimus (rapamycin), tacrolimus (FK506), everolimus (certican), temsirolimus (CCI-779) and zotarolimus (ABT-578).

21. The medical device of claim 13 wherein said medical device is selected from the group consisting of vascular stents, urethral stents, pacemakers, implantable defibrillators, bone screws, guide wires, dental implants, vascular stents, stent grafts, urethral stents, bile duct stents, catheters, pacemaker leads, sutures and prosthetic heart valves.

22. The medical device of claim 13 wherein said textured surface is prepared by a process selected from the group consisting of chemical etching, plasma etching, mechanical etching, and photo-etching.

23. A medical device comprising a textured surface and a biocompatible polymeric coating disposed on said textured surface, wherein said textured surface comprises closely spaced regular grooves forming a geometric pattern, comprising repeating irregularly shaped units having an irregular etch width, and wherein said medical device is selected from the group consisting of vascular stents, urethral stents, pacemakers, implantable defibrillators, bone screws, guide wires, dental implants, vascular stents, stent grafts, urethral stents, bile duct stents, catheters, pacemaker leads, sutures and prosthetic heart valves, wherein said biocompatible coating further comprising at least one bioactive agent and wherein said at least one bioactive agent is selected from the group consisting of sirolimus (rapamycin), tacrolimus (FK506), everolimus (certican), temsirolimus (CCI-779) and zotarolimus (ABT-578).

* * * * *